(12) United States Patent
Hsiung et al.

(10) Patent No.: US 6,974,716 B2
(45) Date of Patent: Dec. 13, 2005

(54) METHOD FOR FABRICATING A TITANIUM NITRIDE SENSING MEMBRANE ON AN EGFET

(75) Inventors: Stephen S. K. Hsiung, Jungli (TW); Jung-Chuan Chou, Yunlin Hsien (TW); Tai-Ping Sun, Jungli (TW); Wen-Yaw Chung, Taoyuan (TW); Yuan-Lung Chin, Junghe (TW); Lei Zhen Ce, Perak (MY)

(73) Assignee: Chung Yuan Christian University, Chung-Li (TW)

( * ) Notice: Subject to any disclaimer, the term of this patent is extended or adjusted under 35 U.S.C. 154(b) by 128 days.

(21) Appl. No.: 10/802,907

(22) Filed: Mar. 17, 2004

(65) Prior Publication Data

US 2004/0185591 A1    Sep. 23, 2004

(30) Foreign Application Priority Data

Mar. 19, 2003   (TW) .............................. 92106067 A

(51) Int. Cl.⁷ ............................................. H01L 21/00
(52) U.S. Cl. ......................................... 438/49; 438/48
(58) Field of Search .................................. 438/5, 48, 49, 438/199

(56) References Cited

U.S. PATENT DOCUMENTS

| | | | | |
|---|---|---|---|---|
| 4,739,380 A | * | 4/1988 | Lauks et al. ................ | 257/253 |
| 5,607,566 A | * | 3/1997 | Brown et al. ............... | 257/414 |
| 6,218,208 B1 | * | 4/2001 | Chou et al. .................. | 438/49 |
| 6,236,075 B1 | * | 5/2001 | Hsiung et al. .............. | 257/252 |
| 6,897,081 B2 | * | 5/2005 | Hsiung et al. .............. | 438/48 |

* cited by examiner

Primary Examiner—Amir Zarabian
Assistant Examiner—Khanh Duong
(74) Attorney, Agent, or Firm—Thomas, Kayden, Horstemeyer & Risley

(57) ABSTRACT

A method for fabricating a titanium nitride (TiN) sensing membrane on an extended gate field effect transistor (EG-FET). The method comprises the steps of depositing a layer of aluminum on a gate terminal of the EGFET using thermal evaporation and forming the TiN sensing membrane on an exposed part of the layer of aluminum in the sensitive window as an ion sensitive sensor (pH sensor) using a radio frequency (RF) sputtering process. Because TiN is suitable for use in a standard CMOS process, all the elements in the sensing device can be mass produced and offer the benefits of low cost, high yield, and high performance.

8 Claims, 11 Drawing Sheets

US 6,974,716 B2

METHOD FOR FABRICATING A TITANIUM NITRIDE SENSING MEMBRANE ON AN EGFET

BACKGROUND OF THE INVENTION

1. Field of the Invention

The present invention relates to a sensing membrane on an ion sensitive field effect transistor (ISFET), and in particular to a method for fabricating a titanium nitride (TiN) sensing membrane on an extended gate field effect transistor (EGFET). The method forms the TiN sensing membrane as an ion sensitive sensor (pH sensor) using a radio frequency (RF) sputtering process and a standard complementary metal oxide semiconductor (CMOS) process. The method uses the standard CMOS process for mass production providing the benefits of low cost, high yield, and high performance.

2. Description of the Related Art

A glass electrode has typically been used as an ion sensing electrode. A glass electrode has the disadvantages of difficulty in measuring miniaturized structures, susceptibility to damage, and low portability. To solve those problems, Piet Bergveld introduced an ion sensitive field effect transistor (ISFET) in 1970. ISFET has the advantages of compatibility with standard CMOS process, high input impedance, and low output impedance, miniaturization capability minute solution measurement, rapid response, and pH measurement capability. Therefore, ISFET has been developed and applied in a variety of fields relating to miniaturized pH sensors and biotechnical sensing devices.

In the 1970s, research on ISFET pH sensors and related applications had just begun. In the 1980s, research on ISFET pH sensors had progressed to a more advanced level regarding aspects of fundamental theories, crucial techniques, and practical applications. Over 30 different ISFETs have been introduced to measure several kinds of ion and chemical materials. Great strides have also been made in miniaturization, modulization, and multi-functionality. According to current research, a hydrogen ion sensing membrane on a gate oxide layer of an ISFET typically comprises silicon dioxide ($SiO_2$), silicon nitride ($Si_3N_4$), tantalum oxide ($Ta_2O_5$), aluminum oxide ($Al_2O_3$), or other materials. These materials have the disadvantages of low linear sensitivity and low photostability, particularly after long-term operation. Additional processes are also required to handle these materials. Due to the described problems, a replacement material is called for.

SUMMARY OF THE INVENTION

Accordingly, an object of the present invention is to provide a method for fabricating a titanium nitride (TiN) sensing membrane on an extended gate field effect transistor (EGFET). The method forms the TiN sensing membrane as an ion sensitive sensor (pH sensor) using a radio frequency (RF) sputtering process and a standard CMOS process. The method uses standard CMOS process for mass production and provides the benefits of low cost, high yield, and high performance.

The TiN sensing membrane has the features of long-term stability with low drift, rapid response time of less than 0.1 second, and high linear sensitivity of approximately 56 to 58 mV/pH due to the Nernst response. The method of the present invention comprises the steps of depositing a layer of aluminum on a gate terminal of the EGFET using thermal evaporation, wherein the layer of aluminum extends from the gate terminal to a sensitive window of the EGFET and forms the TiN sensing membrane on an exposed part of the aluminum layer in the sensitive window as an ion sensitive sensor (pH sensor) using a radio frequency (RF) sputtering process during which TiN is used as a sputtering target and a mixture of argon and nitrogen with a ratio of 9:1 is used as a reactant. A substrate temperature of 150° C., a deposition pressure of 5 milli-torrs, a sputtering duration of 1 hour, and an RF power of 90 watts are suited to an operating condition for forming the TiN sensing membrane. The TiN sensing membrane has a thickness of about 2000 Å.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
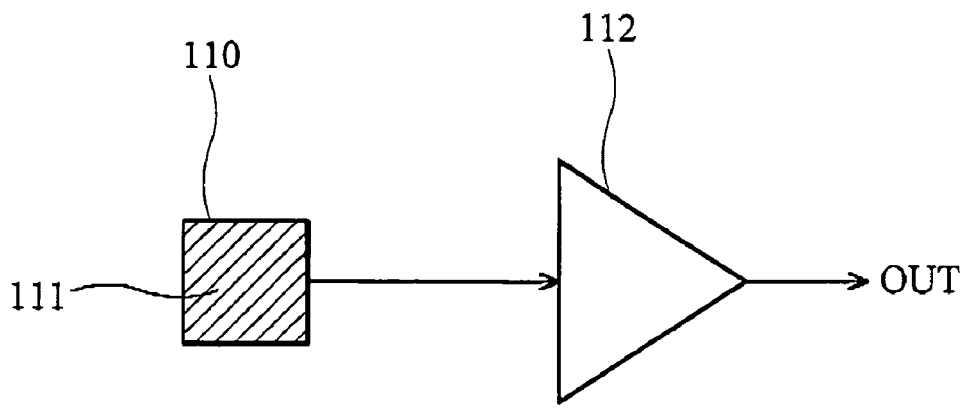
FIG. 1 is a schematic diagram showing an EGFET circuit of the present invention.

FIG. 1 is a schematic diagram showing an EGFET circuit of the present invention. As shown in FIG. 1, a sensing structure including a sensing window 110 and a sensing membrane 111 is immersed in a pH buffer solution to form a electrically conductible circuit by which the pH value sensed by the sensing membrane 111 is output through an output end OUT to an extra readout circuit described hereinafter.

Figure 2:
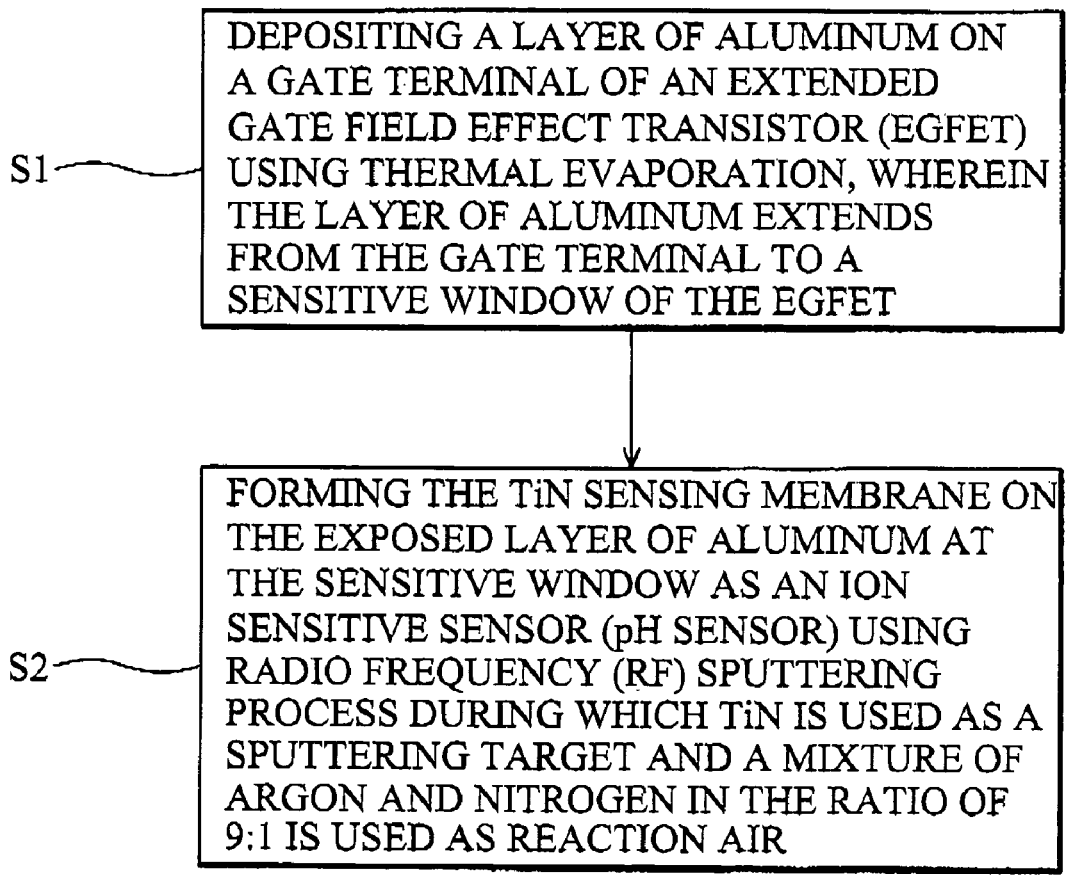
FIG. 2 is a flowchart showing a process of fabricating a TiN sensing membrane of the present invention.

FIG. 2 is a flowchart showing a process of fabricating a TiN sensing membrane of the present invention. As shown in FIG. 2, the method of the present invention comprises the steps of depositing a layer of aluminum on a gate terminal of the EGFET using thermal evaporation, wherein the layer of aluminum extends from the gate terminal to a sensitive window of the EGFET and forming the TiN sensing membrane on an exposed part of the layer of aluminum in the sensitive window as an ion sensitive sensor (pH sensor) using a radio frequency (RF) sputtering process during which TiN is used as a sputtering target and a mixture of argon and nitrogen in the ratio of 9:1 is used as a reactant. A substrate temperature of 150° C., a deposition pressure of 5 milli-torrs, sputtering duration of 1 hour, and an RF power of 90 watts are the preferred operating conditions for forming the TiN sensing membrane. The TiN sensing membrane has a thickness of about 2000 Å. The TiN sensing membrane has features of long-term stability with low drift, rapid response time of less than 0.1 seconds, and high linear sensitivity of approximately 56 58 mV/pH due to the Nernst response. A detailed description of the EGFET is provided in the following.

Figure 3:
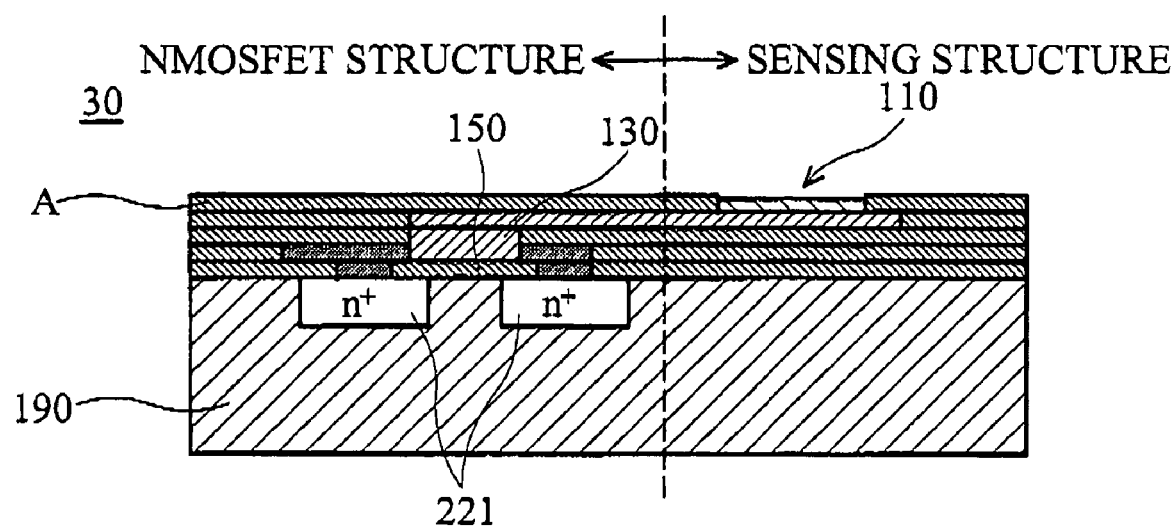
FIG. 3 is a cross-section showing a laminated structure of the EGFET circuit in FIG. 1 of the present invention.

FIG. 3 is a cross-section showing a laminated structure of the EGFET circuit in FIG. 1 of the present invention. As shown in FIG. 3, an EGFET consists essentially of a sensing structure and an N-type metal oxide semiconductor field effect transistor (MOSFET), wherein the sensing structure is the same as previously described and the N-type MOSFET is described in the following.

Figure 4:
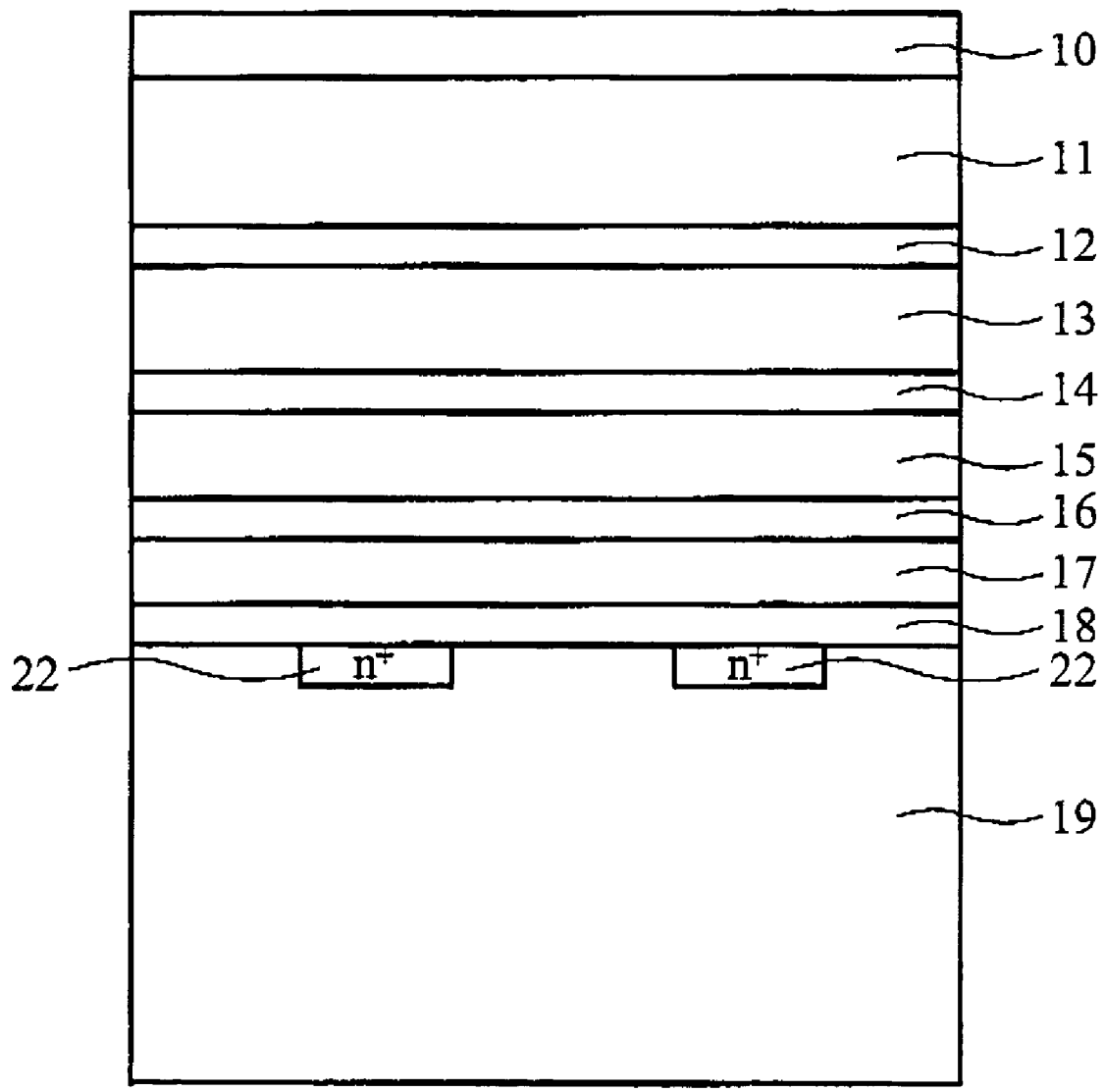
FIG. 4 is a schematic cross-section showing a laminated structure of the EGFET circuit in FIG. 1 of the present invention.

FIG. 4 is a schematic cross-section showing a laminated structure of the EGFET circuit in FIG. 1 of the present invention. FIG. 4 shows cross-sectional layers fabricated by the standard 0.5 μm CMOS integrated circuit (IC), double poly double metal (2P2M), N-type well process. In FIG. 4, in addition to the deposition layers and metal layers produced by the standard CMOS IC process, an N-type diffusion region 22 is also produced by the doping step of the standard process to form the MOSFET structure in FIG. 3. As shown in FIG. 4, the layers included a passivation layer 10 with a 0.7 μm thickness, a metal layer 11 with a 1.1 μm thickness, an oxide layer 12 with a 0.5 μm thickness, a metal layer 13 with a 0.6 μm thickness, an oxide layer 14 with a 0.5 μm thickness, a gate poly-silicon layer 15 with a 0.3 μm thickness, a gate oxide layer 16 with a 135 Å thickness, a capacitance poly-silicon layer 17 with a 0.2 μm thickness, a field effect oxide layer 18 with a 0.5 μm thickness, an N-type metal oxide semiconductor (NMOS) included in an EGPET, disposed over a P-type silicon substrate 19, and having a width to length (W/L) ratio of 600 μm/20 μm, a 300 μm×300 μm sensitive window, and a chip with a total area of 1.8 mm×1.8 mm.

As shown in FIG. 3, the chip includes an N-type MOSFET (NMOSFET), formed by an N-type diffusion region 221 (applying the N-type diffusion region 22 of FIG. 4) and a middle P-type substrate 190 (applying the P-type silicon substrate 19 of FIG. 4), with an extended aluminum structure 130 (applying the metal layer 13 of FIG. 4), using the standard IC process. The layer of aluminum membrane 130 disposed on a gate terminal 150 (applying the gate poly-silicon layer 15 of FIG. 4) extends from the gate terminal to a sensitive window 110 of the EGFET. With the exception of the area directly above the sensitive window 110, the aluminum layer 130 is coated with an insulator, a layer of glass A, to achieve the required NMOSFET structure. Moreover, a TiN sensing membrane 110 (applying the metal layer 11 of FIG. 4) is formed on the sensitive window 110 to produce an EGFET-based chip 30 of the present invention using a sputtering process. The sensitivity of the completed EGFET component is measured to be 56.3 mV/pH, very close to the ideal Nernst response, indicating a highly linear relationship curve between the sensing voltage level and the output voltage. The NMOSFET is the preferred MOSFET structure of the present invention as it has a higher mobility than a PMOSFET.

Figure 5:
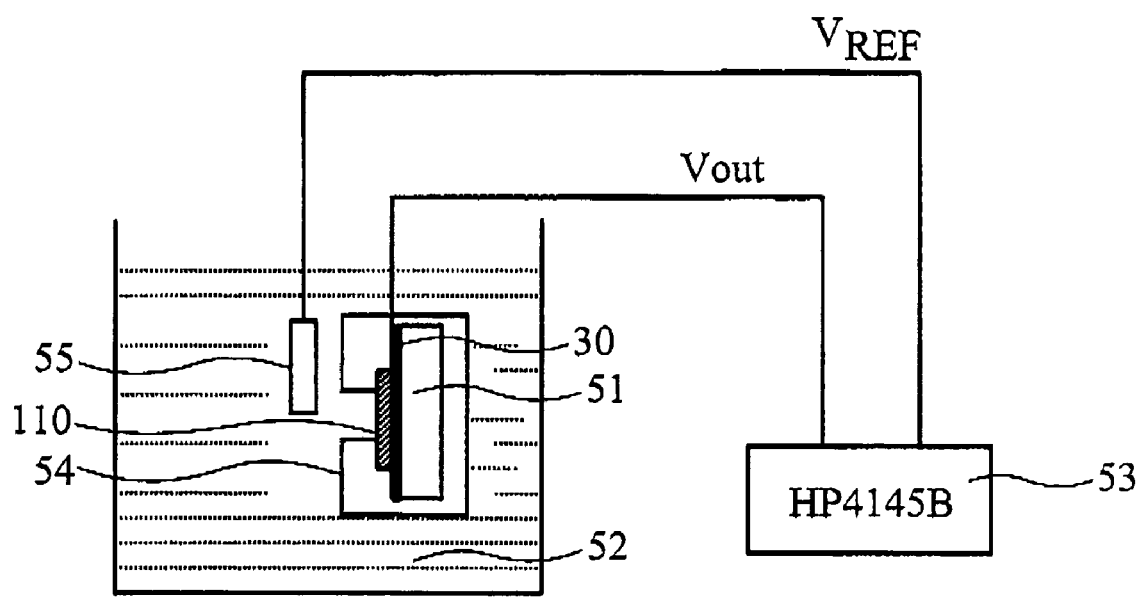
FIG. 5 is a schematic diagram showing a measurement configuration of the present invention.

FIG. 5 is a schematic diagram showing a measurement configuration of the present invention. As shown in FIG. 5, the chip 30 on a ceramic base 51 is encapsulated with epoxy resin (epoxy) to provide electrical insulation for the bonding wires and exposed silicon regions of the chip 30. The encapsulated chip 54 and a reference electrode 55 are immersed in a buffer solution 52 for 1 minute in order to measure and analyze the sensors of the chip 30 through the sensitive window 110 with the TiN sensing membrane 111. In practice, the HP4145B semiconductor parameter analyzer 53 was used to obtain sensor output through the integrated readout circuit via the TiN sensing membrane 111 and refers to the voltage $V_{REF}$ of the reference electrode 55 to generate corresponding output $V_{OUT}$.

Figure 6:
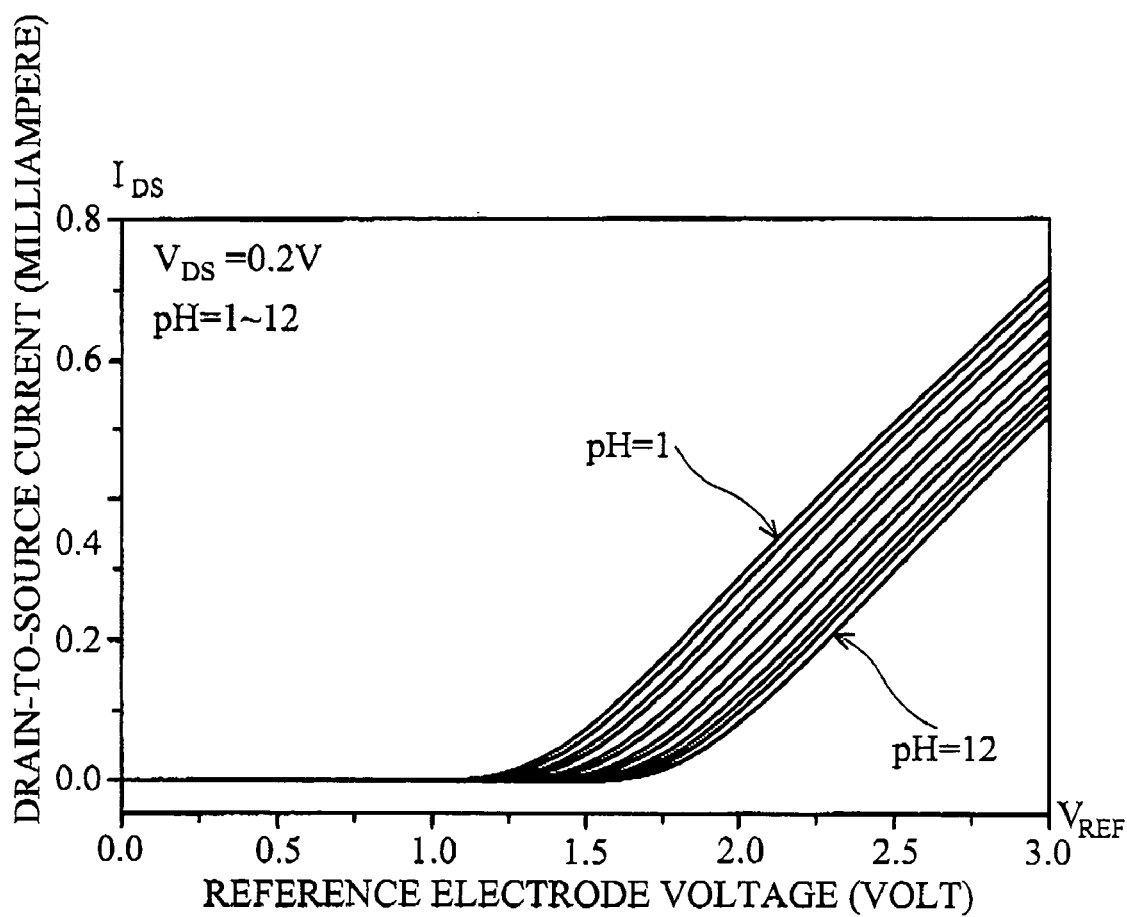
FIG. 6 is a plot showing curves of a sensing current to a reference voltage ($I_{DS}$-$V_{REF}$) under different pH buffer solutions for the EGFET pH sensor in FIG. 5 of the present invention.

FIG. 6 is a plot showing curves of a sensing current to a reference voltage ($I_{DS}$-$V_{REF}$) under different pH buffer solutions for the EGFET pH sensor in FIG. 5 of the present invention. In FIG. 6, the lateral axis is the reference voltage $V_{REF}$ of reference electrode 55 and the vertical axis is the sensing current $I_{DS}$, When a Ag/AgCl-based reference electrode 55 is immersed in the buffer solutions 52 with pH values from 1 to 12 for 1 minute at room temperature and then the measurement is performed under operating conditions, a family of curves can be generated by applying the drain-to-source voltage $V_{DS}$=0.2V for the reference voltage $V_{REF}$. As shown in FIG. 6, the resulting pH values of the solution 92 and the reference voltage $V_{REF}$ are inversely proportional to the current $I_{DS}$, so the measured current $I_{DS}$ goes higher as the pH value becomes smaller. Therefore, the sensing purpose is achieved using the transfer characteristics of the sensing current $I_{DS}$ of which the output value varies significantly according to the pH values of different buffer solutions.

Figure 7:
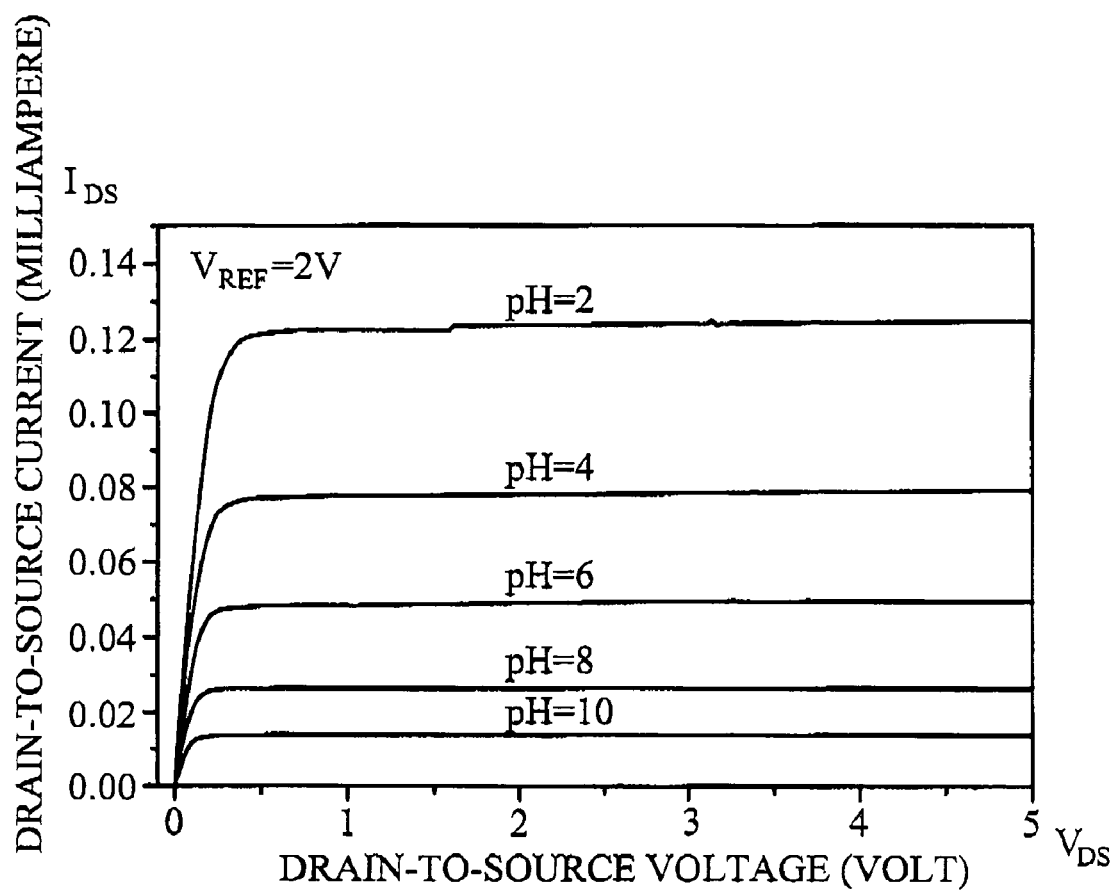
FIG. 7 is a plot showing curves of a sensing current to a sensing voltage ($I_{DS}$-$V_{DS}$) under different pH buffer solutions for the EGFET pH sensor in FIG. 5 of the present invention.

FIG. 7 is a plot showing curves of a sensing current to a sensing voltage ($I_{DS}$-$V_{DS}$) under different pH buffer solutions for the EGFET pH sensor in FIG. 5 of the present invention. As shown in FIG. 7, when a pH sensor is immersed in different pH buffer solutions, the variations between the drain-to-source current $I_{DS}$ and voltage $V_{DS}$ under different pH buffer solutions is detected and analyzed. The result shows that the drain-to-source current varies with the turn-on voltage of the pH buffer solution. When applying the reference electrode voltage $V_{REF}$=2.0V in operation, the drain-to-source voltage $V_{DS}$ fluctuates from 0 to 5V and thus the device is functional in a saturation region. As shown in FIG. 7, the current $I_{DS}$ varies as a function of square root.

Figure 8:
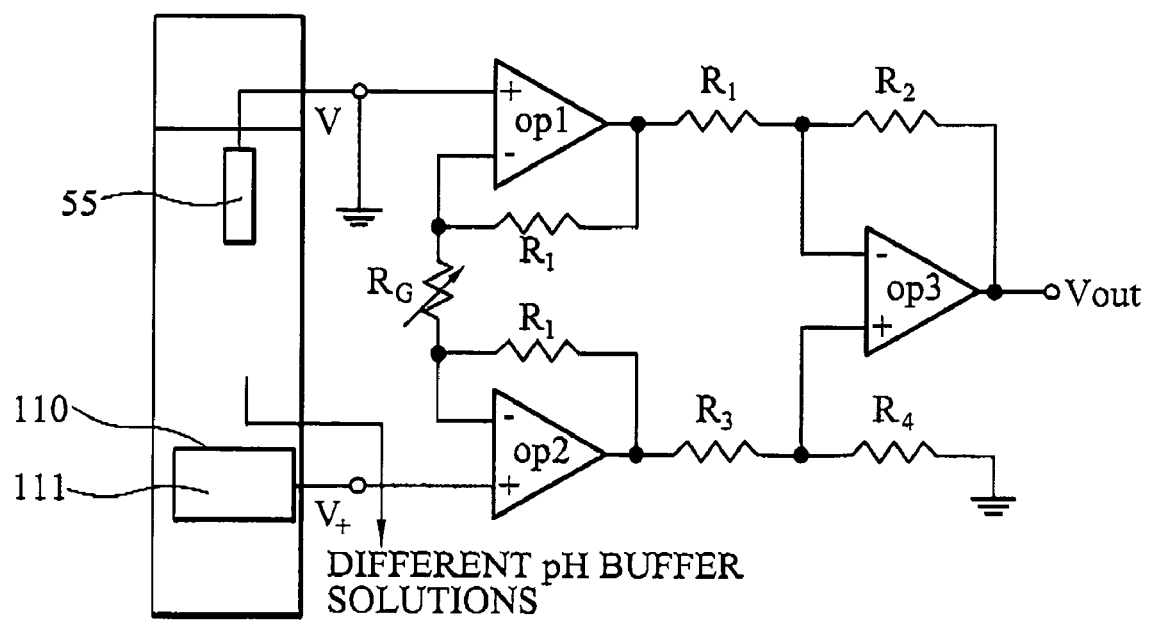
FIG. 8 is a schematic diagram of amplifier meters used as a readout circuit of the present invention.

FIG. 8 is a schematic diagram of amplifier meters used as a readout circuit of the present invention. As shown in FIG. 8, the amplifier meters read the voltage level difference between that of the sensing membrane and that of the reference electrode, and the difference varies according to a pH value in the range of 1 to 12. The initial gain is 2.

Figure 9:
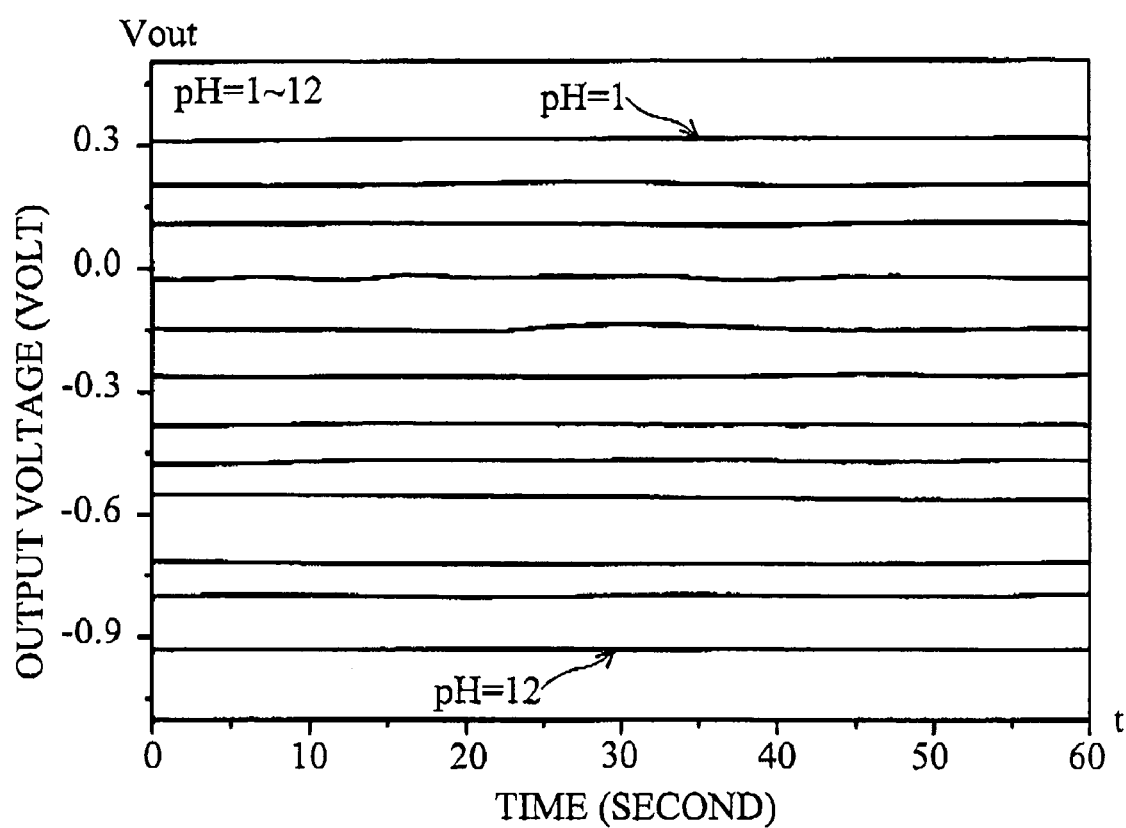
FIG. 9 is a plot showing curves of an output voltage of a pH sensor in FIG. 8 with respect to duration of the present invention.

FIG. 9 is a plot showing curves of an output voltage of a pH sensor in FIG. 8 with respect to time in the present invention. In FIG. 9 the lateral axis is the time t and the vertical axis is the output voltage $V_{OUT}$. Within the measured time of 1 minute, the value of the output voltage $V_{OUT}$ is read for each pH value increasing from 1 to 12 by an increment of 1. As shown in FIG. 9, each value of the output voltage $V_{OUT}$ roughly remains on a fixed value.

Figure 10:
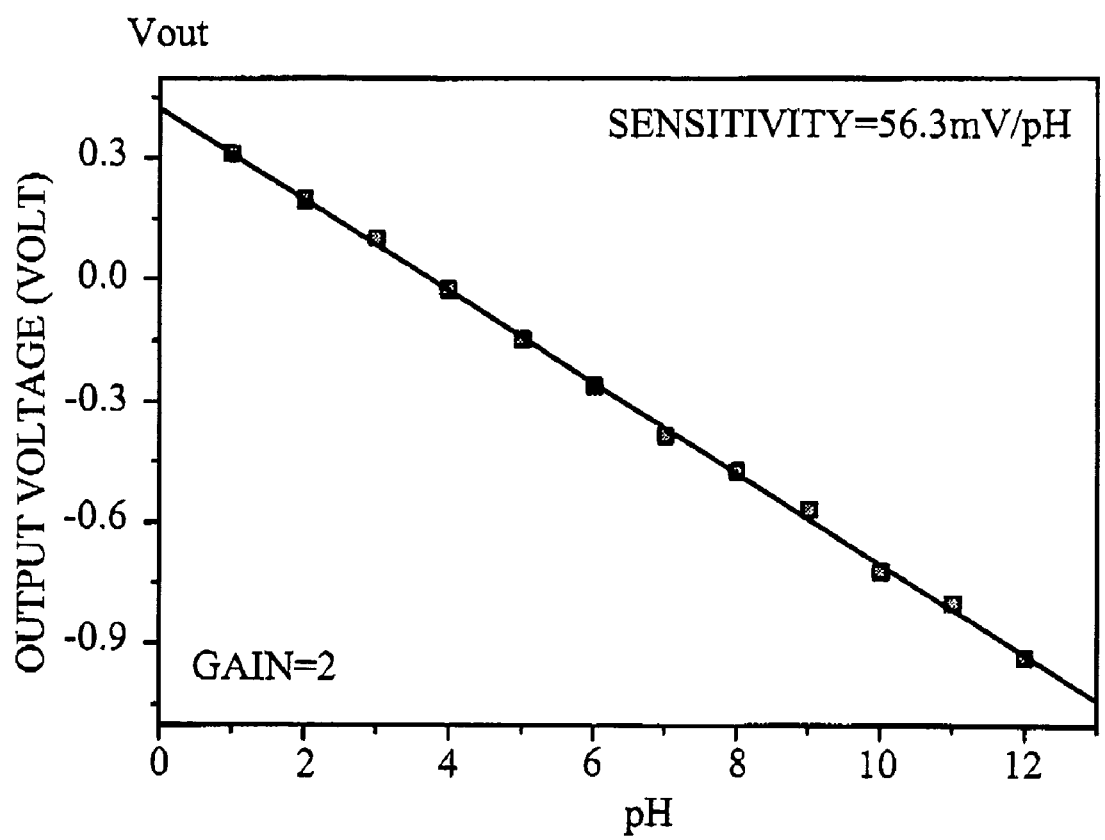
FIG. 10 is a plot showing curves of an output voltage of a pH sensor in FIG. 8 with respect to pH values ($V_{OUT}$-pH) of the present invention.

FIG. 10 is a plot showing curves of an output voltage of a pH sensor in FIG. 8 with respect to pH values ($V_{OUT}$-pH) of the present invention. As shown in FIG. 10, the sensitivity is almost linear and the value is 56.3 mV/pH. This result fulfills the expectation that the TiN sensing membrane has a linear relationship with the output voltage, and high linear sensitivity due to the Nernst response.

Figure 11:
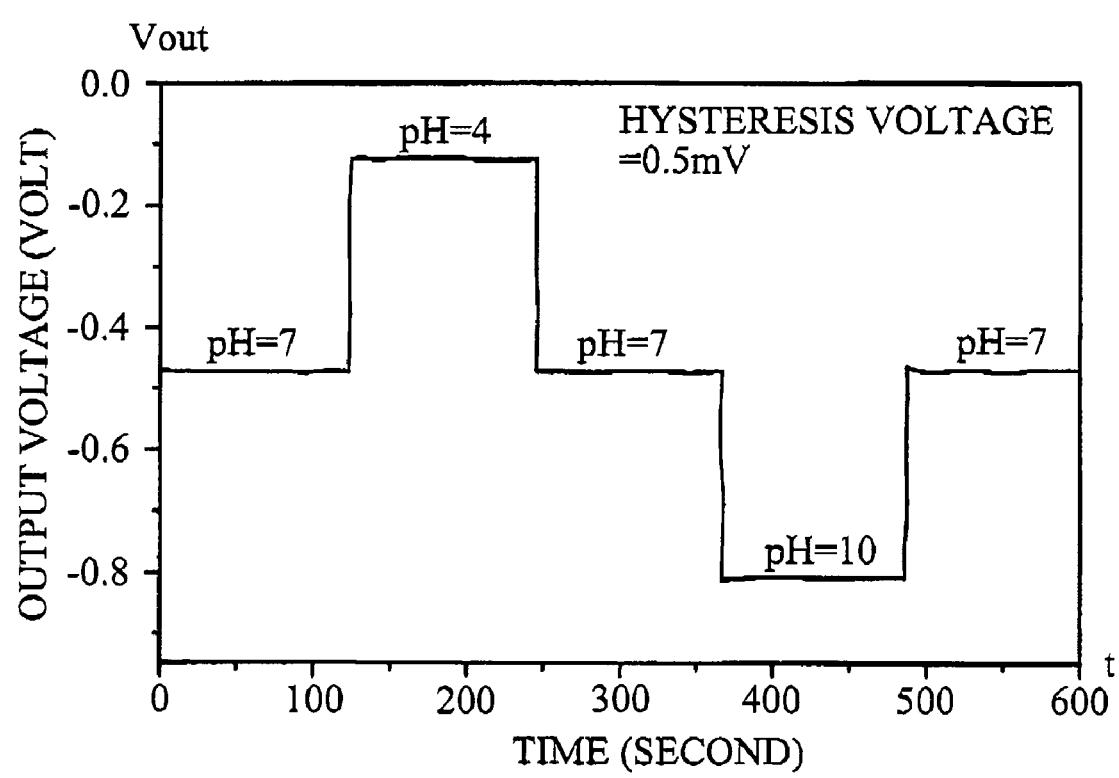
FIG. 11 is a plot showing curves of an output voltage of a pH sensor in FIG. 8 with respect to the duration of hysteresis voltage testing of the present invention.

FIG. 11 is a plot showing curves of an output voltage of a pH sensor in FIG. 8 with respect to time for testing a hysteresis voltage of the present invention. As shown in FIG. 11, a sensing component was immersed in different pH buffer solutions in the sequence of pH=7→4→7→10→7. Each immersion period was 2 minutes. The resulting hysteresis voltage is determined to be 0.5 mV by subtracting the value of the initial voltage from that of the final voltage. This result shows the sensing component has the feature of high reusability.

Figure 12:
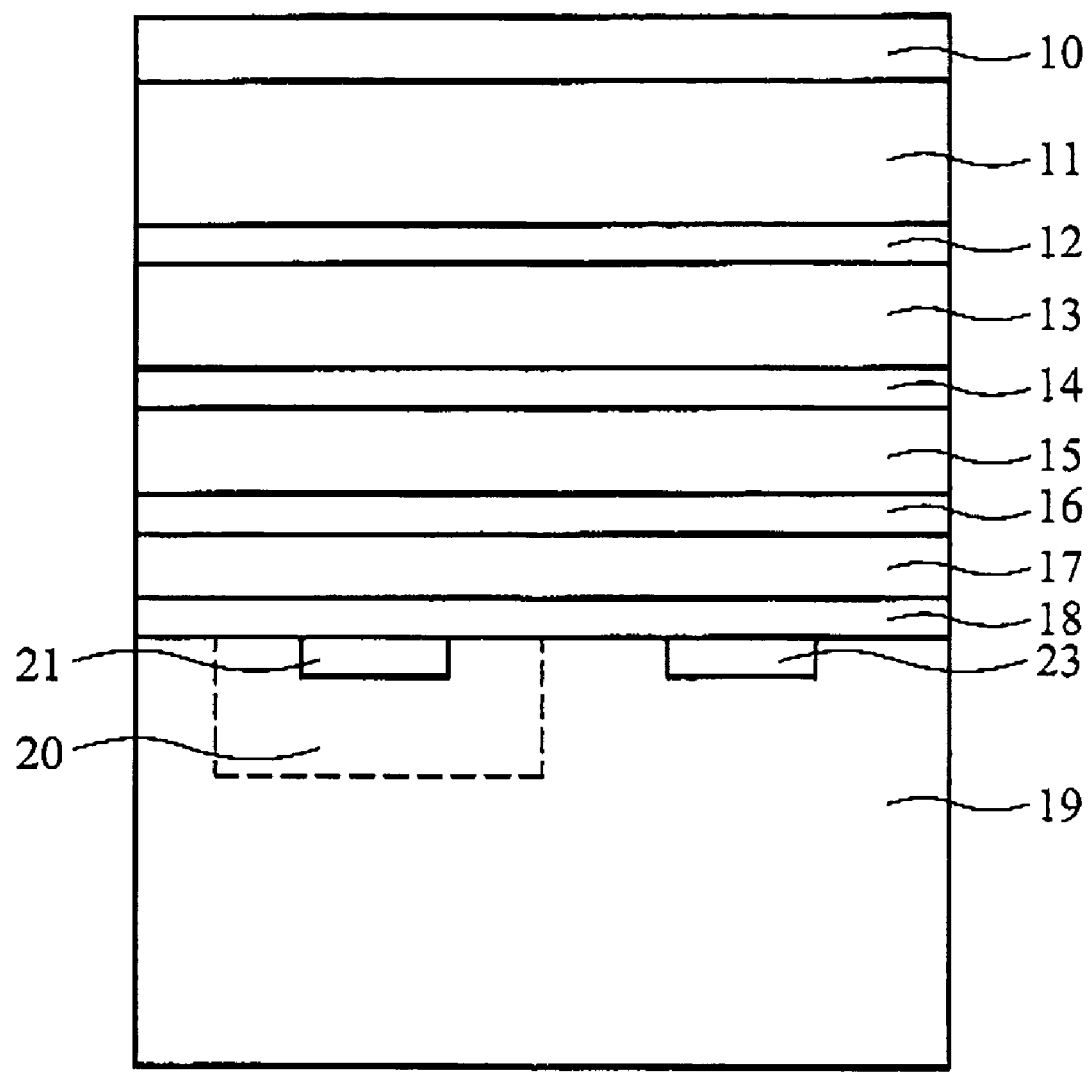
FIG. 12 is a schematic cross-section showing a laminated structure of an EGFET circuit with a temperature sensor and a photosensor of the present invention.

FIG. 12 is a schematic cross-section showing a laminated structure of an EGFET circuit with a temperature sensor and a photosensor of the present invention. As shown in FIG. 12, the TiN sensing membrane can be used in structures comprising single or multiple sensing components. Multiple sensing components including pH sensors, temperature sensors, and photosensors are integrated on a single chip using the standard process for fabricating silicon chips. The structure of the pH sensor is the same as previously described with reference to FIGS. 3 and 4. The temperature sensor is fabricated by forming an N-type well 20 over a P-type substrate 19 and then a P-type diffusion region ($p^+$) 21 within the N-type well 20 using an ion implantation process to form a $p^+$-N diode to sense a temperature by determining a decreased turn-on voltage to be a higher temperature under a forward bias. The photosensor is fabricated by forming an N-type diffusion region ($n^+$) 23 within the P-type substrate 19 using an ion implantation process to form a $n^+$-P diode to sense a photo intensity using the feature that a current caused by changing charge varies with the degree of the photo intensity under a reversed bias. As cited, all sensors including the pH sensor, the temperature sensor, and the photosensor as well as the corresponding readout circuits are fabricated on a single chip using the standard CMOS IC process, and the entire area used by the chip is only about 1.8 mm×1.8 mm including wiring points. Therefore, the chip is suitable for mass production due to the features of low cost and limited physical size. Additionally, the integrated chip can compensate for temperature and optical effects and outputs the desired accurate pH values.

The invention can also be applied to other fields. For example, the described readout circuit can convert a biochemical signal or a physical signal to an electrical signal to be output for measuring the pH value of environmental water, practical for pollution monitors needed by the industry and pH reaction controls needed by the bioindustry.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for fabricating a titanium nitride (TiN) sensing membrane on an extended gate field effect transistor (EGFET), comprising the steps of:
    depositing a layer of aluminum on a gate terminal of the EGFET using thermal evaporation, wherein the layer of aluminum extends from the gate terminal to a sensitive window of the EGFET; and
    forming the TiN sensing membrane on an exposed part of the layer of aluminum in the sensitive window as an ion sensitive sensor (pH sensor) using a radio frequency (RF) sputtering process during which TiN is used as a sputtering target and a mixture of argon and nitrogen in the ratio of 9:1 is used as a reactant.

2. The method as claimed in claim 1, wherein a substrate temperature of 150° C., a deposition pressure of 5 millitorrs, a sputtering duration time of 1 hour, and an RF power of 90 watts are the preferred operating conditions for forming the TiN sensing membrane.

3. The method as claimed in claim 1, wherein the TiN sensing membrane has a thickness of about 1800 to 2900 Å.

4. The method as claimed in claim 1, wherein a gate terminal of the pH sensor is referred to as a reference electrode of the pH sensor.

5. The method as claimed in claim 1, wherein the EGFET includes a temperature sensor and a photosensor.

6. The method as claimed in claim 5 further comprising the steps of:
    forming an N-type well over a P-type substrate and then a P-type diffusion region within the N-type well using an ion implantation process to form a temperature diode consisting of the P-type diffusion region with respect to the N-type well, such that the temperature diode acts as a temperature sensor to sense a temperature under a forward bias; and
    forming an N-type diffusion region within the P-type substrate using an ion implantation process to form a photodiode consisting of the N-type diffusion region with respect to the P-type substrate, such that the photodiode acts as a photosensor to sense a photointensity under a reversed bias.

7. The method as claimed in claim 6, wherein the temperature sensor senses the temperature by determining a decreased turn-on voltage to be a higher temperature under forward bias.

8. The method as claimed in claim 6, wherein the photosensor senses the photo intensity using a feature that a current caused by changing charge varies with the degree of the photointensity under the reversed bias.

* * * * *